United States Patent [19]

Kato

[11] Patent Number: 4,920,230

[45] Date of Patent: Apr. 24, 1990

[54] METHOD OF PRODUCING NITROGEN-CONTAINING HETEROAROMATIC COMPOUNDS HAVING AN ALKOXY GROUP

[75] Inventor: Masayasu Kato, Hyogo, Japan

[73] Assignee: Takeda Chemical Industries, Ltd., Higashi, Japan

[21] Appl. No.: 209,374

[22] Filed: Jun. 21, 1988

[30] Foreign Application Priority Data

Jun. 29, 1987 [JP] Japan ................................ 62-161899

[51] Int. Cl.$^5$ .......................................... C07D 213/62
[52] U.S. Cl. .................................... 546/290; 544/239; 544/408; 546/298; 546/303
[58] Field of Search ......................... 546/290, 298, 303

[56] References Cited

U.S. PATENT DOCUMENTS

| 3,655,679 | 4/1972 | Shen | 546/269 |
| 4,120,692 | 10/1978 | Plant | 546/303 |
| 4,214,086 | 7/1980 | Fäh | 546/290 |
| 4,271,304 | 6/1981 | Edington et al. | 546/290 |
| 4,595,763 | 6/1986 | Renga et al. | 546/290 |
| 4,609,732 | 9/1986 | Plummer | 546/269 |
| 4,620,008 | 10/1986 | Brandstrom et al. | 546/290 |

FOREIGN PATENT DOCUMENTS 69126 11/1968 Fed. Rep. of Germany .
2134523 8/1984 United Kingdom .

OTHER PUBLICATIONS

Starks et al., "Phase Transfer Catalysis", Academic Press, New York, (1978), pp. 8-9, 12, 24-25.
Chemical Abstracts, vol. 45, No. 5152e.
Chemical Abstracts, vol. 72, 1970, p. 379, No. 90309w.
Montanari et al., Chemical Abstracts, vol. 97, 1982, p. 669, 16248r.
Montanari et al., "One-Step Synthesis of m-nitroanisole from m-dinitrobenzene under Solid-Liquid Phase-Transfer Conditions", Chem. & Ind., 1982, p. 412.
Synthesis, No. 7, Jul. 1980, p. 573-p. 575, "Phase-Transfer Mediated Heteroaromatic Nucleophilic substitution: Introduction of a Beta-Adrenergic Blocking Moiety".
Ballesteros et al., "Study of the Catalytic Properties of tris(3,6-dioxaheptyl)amine (TDA-1) in Heteroaromatic Nucleophilic Substitution of Chloropyridines and Their N-Oxides", Tetrahedron, vol. 43, No. 11, 1987, pp. 2557-2565.

Primary Examiner—Donald G. Daus
Attorney, Agent, or Firm—Wegner & Bretschneider

[57] ABSTRACT

Nitrogen-containing heteroaromatic compounds having an alkoxy group can be produced by reacting nitrogen-containing heteroaromatic compounds having a nitro group with alcohol or alcoholate in the presence of a phase transfer catalyst and a base.

7 Claims, No Drawings

METHOD OF PRODUCING NITROGEN-CONTAINING HETEROAROMATIC COMPOUNDS HAVING AN ALKOXY GROUP

This invention relates to a method of producing nitrogen-containing heteroaromatic compounds having an alkoxy group.

Nitrogen-containing heteroaromatic compounds having an alkoxy group are useful as starting materials for the synthesis of drugs. Among said compounds, for example, alkoxypyridine-1-oxides are useful as advantageous starting materials for the synthesis of 2-(2-pyridylmethylsulfinyl)benzimidazole compounds or 2-(2-pyridylmethylthio)benzimidazole compounds, which are useful as antiulcer agents (cf. U.S. Pat. No. 4255431, European Patent Publications Nos. 45200, 74341, 80602, 5129, 174726 and 175464, and Laid-open British Patent Specification No. 2134523A).

It is known that alkoxypyridine-1-oxides can be produced by reacting a nitropyridine-1-oxide with an alcohol in the presence of a base. Thus, for example, mention may be made of the method of producing 4-methoxypyridine-1-oxide which comprises reacting 4-nitropyridine-1-oxide with sodium methoxide in methanol [cf. Yakugaku Zasshi, 63, 265 (1943)], the method of producing 4-ethoxypyridine-1-oxide which comprises reacting 4-nitropyridine-1-oxide with ethanol in the presence of potassium carbonate at elevated temperatures [cf. East German Patent No. 69,126] and the method of producing 2,3-dimethyl-4-(2,2,3,3-tetrafluoropropoxy)pyridine-1-oxide which comprises reacting 2,3-dimethylpyridine-1-oxide with 2,2,3,3-tetrafluoropropanol in the presence of t-butoxypotassium at elevated temperatures [cf. European Patent Publication No. 174726].

However, problems are encountered in carrying out these methods; for example, decomposition of the starting material or product is significant and the yield is low, or a very long reaction period (20–50 hours) is required.

The present inventors made intensive investigations in an attempt to develop a method of producing nitrogen-containing heteroaromatic compounds having an alkoxy group from nitrogen-containing heteroaromatic compounds having a nitro group in good yields and in a short reaction period. As a result, they found that when a relatively weak base, such as potassium carbonate, is used in the presence of a phase transfer catalyst, nitrogen-containing heteroaromatic compounds having an alkoxy group can be obtained from nitrogen-containing heteroaromatic compounds having a nitro group in good yields and in a short reaction period, and have now completed the present invention.

Thus, the present invention is concerned with a method of producing a nitrogen-containing heteroaromatic compound having an alkoxy group of the formula (III)

$$\text{Het} - \text{OR} \qquad \text{(III)}$$

wherein Het is a nitrogen-containing heteroaromatic ring which may be substituted and wherein the nitrogen atom may be oxidized, and R is alkyl, halogenated alkyl, aryl or aralkyl, which comprises reacting a nitrogen-containing heteroaromatic compound having a nitro group of the formula (I)

$$\text{Het-NO}_2 \qquad \text{(I)}$$

wherein Het is as defined above, with a compound of the formula (II)

$$\text{ROM} \qquad \text{(II)}$$

wherein R is as defined above and M is hydrogen or alkali metal, in the presence of a phase transfer catalyst and a base.

Referring to the above formulas, as the nitrogen-containing heteroaromatic ring, for example, an unsaturated 5-or 6-membered ring having one or two nitrogen atom(s) as a hetero atom and wherein the nitrogen atom(s) being optionally oxidated, such as 2H-pyrrole, pyrrole, imidazole, pyrazole, pyridine, pyridine-1-oxide, pyrazine, pyrimidine or pyridazine, can be used.

As the nitrogen-containing heteroaromatic ring, pyridine-1-oxide is preferable.

As the substituent group on the nitrogen-containing heteroaromatic ring can be used, for example, $C_{1-8}$ alkyl, $C_{1-8}$ alkoxy, halogen (e.g. Cl, F, etc.) carboxyl.

Next, the method according to the present invention is described in detail by illustrating a method of producing alkoxypyridine-1-oxides from nitropyridine-1-oxides.

The alkoxypyridine-1-oxides of the formula (III)′

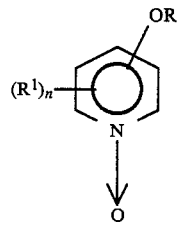

wherein R is as defined above, $R^1$ is alkyl, alkoxy, carboxyl or halogen and n is an integer of 0 to 4 and wherein, when n is 2 or more, $R^1$ may be the same or different, can be produced by reacting a nitropyridine-1-oxide of the formula (I)′

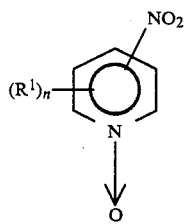

wherein $R^1$ and n are as defined above, with a compound (II) in the presence of a phase transfer catalyst and a base.

Referring to the above formulas, the alkyl represented by $R^1$ is preferably alkyl of 1–8 carbon atoms, such as methyl, ethyl, propyl, isopropyl, butyl, isobutyl, pentyl, hexyl, heptyl or octyl, and more preferably alkyl of 1–4 carbon atoms. The alkoxy represented by $R^1$ is preferably alkoxy of 1–8 carbon atoms, such as methoxy, ethoxy, propoxy, isopropoxy, butoxy, isobutoxy, pentyloxy, hexyloxy, heptyloxy or octyloxy, and more preferably alkoxy of 1–4 carbon atoms. The halogen represented by $R^1$ is, for example, chlorine or fluorine. In the compounds (I)′ and (III)′, the substituent or substituents represented by $R^1$ are preferably located at the 2- or/and 3-positions of the pyridine oxide nucleus.

As the alkyl represented by R, there may be mentioned alkyl groups of 1-8 carbon atoms, preferably 1-4 carbon atoms, such as mentioned above for the alkyl represented by $R^1$. As the halogen in the halogenated alkyl represented by R, there may be mentioned fluorine, bromine, chlorine and iodine, among which fluorine is preferred. As the alkyl in said halogenated alkyl, there may be mentioned alkyls of 1-8 carbon atoms, preferably 1-5 carbon atoms, such as mentioned above for the alkyl represented by $R^1$. Particularly preferred halogenated alkyl species are alkyls of 1-5 carbon atoms which have 3-8 fluorine atoms as substituents, for example trifluoromethyl, 2,2,2-trifluoroethyl, 2,2,3,3,3-pentafluoropropyl, 2,2,3,3-tetrafluoropropyl, 1-(trifluoromethyl)-2,2,2-trifluoroethyl, 2,2,3,3,4,4,4-heptafluorobutyl and 2,2,3,3,4,4,5,5-octafluoropentyl. The aryl represented by R is preferably of 6-14 carbon atoms and is, for example, phenyl, tolyl, xylyl, biphenylyl, naphthyl, anthryl or phenanthryl. The aralkyl represented by R is preferably a group derived from such aryl as mentioned above and alkyl of 1-3 carbon atoms and is, for example, benzyl, phenethyl or 3-phenylpropyl.

From the advantageous production viewpoint, the nitro group in compound (I)' and the alkoxy group represented by OR in compound (III)' should preferably be located in the position 4 or 6.

Referring to the compound of the formula (III)', particularly preferred is that case in which $R^1$ is methyl, n is 2, R is 2,2,2-trifluoroethyl and $R^1$ groups are located in the positions 2 and 3.

The alkali metal represented by M in the formula ROM given above is, for example, lithium, sodium or potassium; sodium is preferred among others.

The base to be used in the present invention includes, among others, alkali metals, such as lithium, sodium and potassium, alkali metal hydrides, such as sodium hydride and potassium hydride, alcoholates, such as t-butoxypotassium and propoxysodium, alkali metal carbonates and hydrogen carbonates, such as potassium carbonate, sodium carbonate, potassium hydrogen carbonate and sodium hydrogen carbonate, and alkali metal hydroxides, such as sodium hydroxide and potassium hydroxide. Preferred among them are alkali metal carbonates and hydrogen carbonates, such as potassium carbonate, sodium carbonate, potassium hydrogen carbonate and sodium hydrogen carbonate. The base is used generally in an amount of about 1-10 moles, preferably about 1-3 moles, per mole of the nitropyridine-1-oxide. The amount of the base is not limited to the range mentioned above, however.

As the phase transfer catalyst to be used in carrying out the reaction in accordance with the invention, there may be mentioned quaternary ammonium salts, such as tetrabutylammonium chloride and benzyltributylammonium chloride, quaternary phosphonium salts, such as tetrabutylphosphonium chloride and tetraphenylphosphonium bromide, crown ethers, such as dibenzo-18-crown-6 and dicyclohexyl-18-crown-6, cryptands, such as [2,2,2]-cryptate, and so forth. Preferred among them are quaternary ammonium salts such as tetrabutylammonium bromide and benzyltributylammonium chloride. These phase transfer catalysts can be used either singly or in admixture. The phase transfer catalyst is used generally in an amount of about 1-20 mole percent, preferably about 5-10 mole percent, based on the nitropyridine-1-oxide. Its amount is not specifically limited to the above range, however.

As the solvent to be used in carrying out the reaction, there may be mentioned the compounds represented by the formula ROH, wherein R is as defined above, in addition, ethers, such as tetrahydrofuran and dioxane, ketones, such as acetone and methyl ethyl ketone, acetonitrile, dimethylformamide, hexamethylphosphoric triamide, and so forth. Preferably, however, the ROH itself, acetone or acetonitrile is used. These solvents may be used either singly or in admixture. When a quaternary ammonium salt is used in the form of an aqueous solution, there may be present a small amount of water in the reaction system. The solvent is used generally in an amount of about 0.5-5 ml, preferably about 1-2 ml, per millimole of the nitropyridine-1-oxide. The solvent amount is not limited to this range in any particular way, however.

The reaction is carried out at a temperature within a wide range from a temperature attained by ice cooling to the vicinity of the boiling point of the solvent used, generally at room temperature to the vicinity of the boiling point of the solvent. The reaction period is generally about 1-15 hours, preferably about 5-10 hours, but is not limited to such range.

After reaction, the desired alkoxypyridine-1-oxides produced by the reaction mentioned above can be isolated and purified, after removal of the solid matter and concentration, by conventional means such as recrystallization, chromatography, etc.

Now, the method of producing the starting compounds (I) is described.

Among the compounds (I), those in which n is 0 are known [cf. Arnold Weissberger et al., The Chemistry of Heterocyclic Compounds, Part 2, pages 97-153, Interscience Publishers, Inc., New York, 1961], while those in which $n=1-4$ are either described in the above-cited reference or producible by nitrating the corresponding pyridine-1-oxides modified beforehand with a group or groups represented by $R^1$, as described in said reference.

In addition, the compound (I) other than the compound (I') can be produced by the method as described in said reference.

When the method according to this invention is used, heteroaromatic compounds having an alkoxy group can be produced in good yields in a short period of time.

The following examples are further illustrative of the method according to the invention.

Example 1

2,3-Dimethyl-4-nitropyridine-1-oxide (5 g) was dissolved in methanol (30 ml). To the solution were added tetrabutylammonium bromide (0.5 g) and potassium hydrogen carbonate (5.6 g), and the mixture was heated (temperature 80°-85° C.) under reflux with stirring for 10 hours. The solid matter was removed from the reaction mixture by filtration, and the filtrate was concentrated and applied to a silica gel (100 g) column. Elution with methanol-dichloromethane (1:9) and recrystallization from ethyl acetate-hexane gave 4.3 g of white 2,3-dimethyl-4-methoxypyridine-1-oxide. Melting point 85°-86° C.

Example 2

The following alkoxypyridine-1-oxides were produced in the same manner as in Example 1.

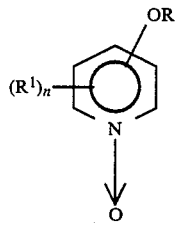

| n | R¹ | R | Melting point (°C.) |
|---|---|---|---|
| 0 | | 4-CH₃ | 80–82 |
| 0 | | 4-C₂H₅ | 125–126 |
| 1 | 2-CH₃ | 4-CH₃ | 85–86 |
| 1 | 2-CH₃ | 4-C₂H₅ | 77–78 |
| 1 | 2-Cl | 4-CH₃ | 99–100 |
| 1 | 2-COOH | 4-CH₃ | 142–144 |

Example 3

2,3-Dimethyl-4-nitropyridine-1-oxide (5 g) was dissolved in acetonitrile (50 ml). To the solution were added 2,2,2-trifluoroethanol (8.7 ml), 50% aqueous solution (1 ml) of benzyltributylammonium chloride and potassium carbonate (12 g), and the mixture was heated (temperature 80°–85° C.) with stirring for 8 hours. The reaction mixture was removed of the solid matter by filtration, concentrated and applied to a silica gel (100 g) column. Elution with methanol-dichloromethane (1:9) and recrystallization from ethyl acetatehexane gave 6.3 g of 2,3-dimethyl-4-(2,2,2-trifluoroethoxy)puridine-1-oxide as white needles. Melting point 138°–139° C.

EXAMPLE 4

The following alkoxypyridine-1-oxide were produced in the same manner as in Example 3.

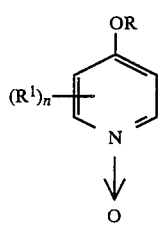

| n | R¹ | R | Melting point (°C.) |
|---|---|---|---|
| 2 | 2-CH₃, 3-CH₃ | 6-CH₂CF₃ | 65–66 |
| 2 | 2-CH₃, 3-CH₃ | 4-CH(CH₃)₂ | Oily* |
| 0 | | 4-CH₂CF₃ | 148–150 |
| 0 | | 4-CH₂φ | 159–161 |
| 1 | 2-CH₃ | 4-φ | 161–162 (Hydrochloride) |

*Infrared absorption spectrum (Neat): Main absorption peaks at 2960, 1615 and 1250 (cm⁻¹)

Example 5

2,3-Dimethyl-4-nitropyridine-1-oxide (5 g) was dissolved in acetonitrile (30 ml). To the solution were added 2,2,2-trifluoroethanol (8.7 ml), tetra-n-butylphosphonium bromide (0.5 g) and potassium carbonate (8.2 g), and the mixture was heated (80°–85° C. with stirring for 7 hours.

The reaction mixture was worked up in the same manner as in Example 3 to give 6.1 g of 2,3-dimethyl-4-(2,2,2-trifluoroethoxy)pyridine-1-oxide as white needles. Melting point 138°–139° C.

Example 6

The procedure of Example 5 was followed by using 18-crown-6 (0.4 g) instead of tetra-n-butylphosphonium bromide. From 2,3-dimethyl-4-nitropyridine-1-oxide (5 g), there was obtained 6.2 g of 2,3-dimethyl-4-(2,2,2-trifluoroethoxy)pyridine-1-oxide. Melting point 138°–139° C.

Reference example 2,3-Dimethylpyridine(40g) was dissolved in glacial acetic acid(80ml). To the solution was added 35% hydrogen peroxide(46.5g), and the mixture was heated at 100°–110° C. to be reacted under reflux with stirring for 3 hours. After the reaction, to the reaction solution was added pformaldehyde(1.5 g); the mixture was heated at 100°–105° C. to decompose the residual hydrogen peroxide and then was concentrated to give 2,3-dimethylpyridine-1-oxide.

The 2,3-dimethylpyridine-1-oxide was dissolved in conc. sulfuric acid (46ml). To the solution was added dropwise a mixture of 98% nitric acid(48ml) and conc. sulfuric acid (67 ml) at 60° to 70° C. taking about an hour and the solution was allowed to react at the temperature for 4 hours.

The reation solution was poured into ice water (750ml) and neutralized with 30% sodium hydroxide below 40° C. The mixture was extracted with dichloromethane(400 ml and 200 ml), and the extract was washed with water(200 ml) and concentrated. By recrystallization from the obtained residue using toluene (100 ml), 2,3-dimethyl-4-nitropyridine-1-oxide (51.5 g) was obtained. M.p. 91°–93° C.

What is claimed is:

1. A method of producing a compound of the formula

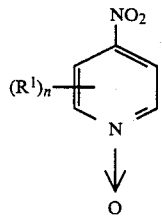

wherein R is C₁₋₈ alkyl, C₁₋₈ alkyl halogenated with fluorine, bromine, chlorine or iodine, C₆₋₁₄ aryl or aralkyl which is derived from C₆₋₁₄ aryl and C₁₋₃ alkyl, R¹ is C₁₋₈ alkyl, C₁₋₈ alkoxy, carboxyl or halogen, and n is an integer from 0 to 4, which comprises:

reacting a compound of the formula wherein R¹ and n are defined above,
with a compound of the formula

ROM wherein R is as defined above, and M is alkali metal, in the presence of a phase transfer catalyst selected from the group consisting of quaternary ammonium salt, quaternary phosphonium salt, crown ether, cryptand and mixtures thereof, and a base selected from the group consisting of alkali metal, alkali metal hydride, alcoholate, alkali metal carbonate, alkali metal hydrogen carbonate and alkali metal hydroxide.

2. A method according to claim 1, wherein the alkali metal M is lithium, sodium or potassium.

3. A method according to claim 1, wherein the quaternary ammonium salt is tetrabutylammonium chloride, tetrabutylammonium bromide or benzyltributylammonium chloride, the quaternary phosphonium salt is tetrabutylphosphonium chloride or tetraphenylphosphonium bromide, the crown ether is dibenzo-18-crown-6, dicyclohexyl-18-crown-6 or 18-crown-6, and the cryptand is [2,2,2]-cryptate.

4. A method according to claim 1, wherein the alkali metal is lithium, sodium or potassium, the alkali metal hydride is sodium hydride or potassium hydride, the alkali metal carbonate is potassium carbonate or sodium carbonate, the alkali metal hydrogen carbonate is potassium hydrogen carbonate or sodium hydrogen carbonate, and the alkali metal hydroxide is potassium hydroxide or sodium hydroxide.

5. A method according to claim 1, wherein the phase transfer catalyst is used in an amount of about 1–20 mole percent based on the compound of the formula

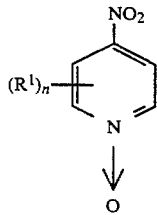

6. A method according to claim 1, wherein the base is used in an amount of about 1–10 mole percent based on the compound of the formula

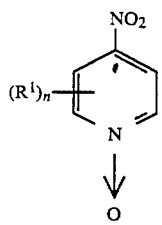

7. A method according to claim 1, wherein the compound of the formula

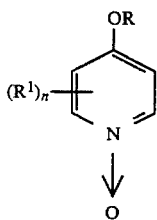

is 2,3-dimethyl-4-(2,2,2-trifluoroethoxy)pyridine-1-oxide, the compound of the formula

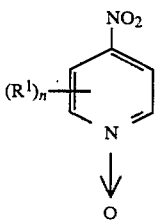

is 2,3-dimethyl-4-nitropyridine-1-oxide, and the compound of the formula

ROM is 2,2,2-trifuloroethanol.

* * * * *